(12) United States Patent
Wei et al.

(10) Patent No.: US 11,491,009 B2
(45) Date of Patent: Nov. 8, 2022

(54) ANNULAR AUGMENTATION DEVICE FOR CARDIAC VALVE REPAIR

(71) Applicant: EVALVE, INC., Santa Clara, CA (US)

(72) Inventors: Michael F. Wei, Redwood City, CA (US); Chad J. Abunassar, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 0 days.

(21) Appl. No.: 17/369,685

(22) Filed: Jul. 7, 2021

(65) Prior Publication Data

US 2021/0330454 A1 Oct. 28, 2021

Related U.S. Application Data

(63) Continuation of application No. 17/200,379, filed on Mar. 12, 2021, which is a continuation of application No. 15/629,505, filed on Jun. 21, 2017, now Pat. No. 10,945,842.

(60) Provisional application No. 62/371,080, filed on Aug. 4, 2016.

(51) Int. Cl.
*A61F 2/24* (2006.01)

(52) U.S. Cl.
CPC ............ *A61F 2/246* (2013.01); *A61F 2/2454* (2013.01); *A61F 2/2463* (2013.01); *A61F 2/2466* (2013.01); *A61F 2210/0014* (2013.01); *A61F 2210/0076* (2013.01); *A61F 2220/0008* (2013.01); *A61F 2220/0016* (2013.01); *A61F 2240/001* (2013.01); *A61F 2250/0098* (2013.01)

(58) Field of Classification Search
CPC ............ A61F 2/24; A61F 2/246; A61F 2/2454
See application file for complete search history.

(56) References Cited

U.S. PATENT DOCUMENTS

| 2003/0199975 A1 | 10/2003 | Gabbay |
| 2005/0038509 A1 | 2/2005 | Ashe |
| 2015/0119981 A1 | 4/2015 | Khairkhahan et al. |
| 2016/0045314 A1 | 2/2016 | Keren et al. |

FOREIGN PATENT DOCUMENTS

WO   WO/2015/020971   2/2015

OTHER PUBLICATIONS

U.S. Appl. No. 17/200,379, filed Mar. 12, 2021.
(Continued)

*Primary Examiner* — Matthew W Schall
(74) *Attorney, Agent, or Firm* — Baker Botts L.L.P.

(57) ABSTRACT

The present disclosure relates to repair devices for repair of regurgitant mitral valves. A repair device includes a body having a perimeter defining an upper side and a lower side. An annular groove is disposed along a posterior section of the perimeter of the device and is configured to receive posterior rim tissue of a mitral valve annulus. First and second anchors extend from the body in an anterior direction. The first and second anchors are configured to engage with respective commissures of the mitral valve to assist in securing the repair device in position. The repair device is structured to minimize or eliminate imparting or transmitting radially outward forces along an anterior section so as to avoid imparting forces to the septum to avoid hindering the function of the aortic valve and the left ventricular outflow tract.

14 Claims, 10 Drawing Sheets

(56) References Cited

OTHER PUBLICATIONS

U.S. Appl. No. 15/629,505 (U.S. Pat. No. 10,945,842), filed Jun. 21, 2017 (Mar. 16, 2021).
U.S. Appl. No. 15/629,505, Feb. 12, 2021 Issue Fee Payment.
U.S. Appl. No. 15/629,505, Nov. 16, 2020 Notice of Allowance.
U.S. Appl. No. 15/629,505, Mar. 11, 2020 Applicant Initiated Interview Summary.
U.S. Appl. No. 15/629,505, Feb. 18, 2020 Request for Continued Examination (RCE).
U.S. Appl. No. 15/629,505, Feb. 18, 2020 Response after Final Action.
U.S. Appl. No. 15/629,505, Nov. 18, 2019 Final Office Action.
U.S. Appl. No. 15/629,505, Jul. 31, 2019 Response to Non-Final Office Action.
U.S. Appl. No. 15/629,505, Mar. 2, 2019 Non-Final Office Action.
U.S. Appl. No. 15/629,505, Jan. 23, 2019 Response to Restriction Requirement.
U.S. Appl. No. 15/629,505, Nov. 29, 2018 Restriction Requirement.

ANNULAR AUGMENTATION DEVICE FOR CARDIAC VALVE REPAIR

CROSS-REFERENCE TO RELATED APPLICATIONS

This application is a continuation of U.S. patent application Ser. No. 17/200,379, filed Mar. 12, 2021, which is a continuation of U.S. patent application Ser. No. 15/629,505, filed Jun. 21, 2017, now U.S. Pat. No. 10,945,842, which claims priority to and the benefit of U.S. Provisional Patent Application Ser. No. 62/371,080, filed Aug. 4, 2016 and titled "ANNULAR AUGMENTATION DEVICE FOR CARDIAC VALVE REPAIR," the disclosure of all of which are incorporated herein by this reference in their entireties.

BACKGROUND

The mitral valve controls blood flow from the left atrium to the left ventricle of the heart, preventing blood from flowing backwards from the left ventricle into the left atrium so that it is instead forced through the aorta for distribution throughout the body. A properly functioning mitral valve opens and closes to enable blood flow in one direction. However, in some circumstances the mitral valve is unable to close properly, allowing blood to regurgitate back into the atrium. Such regurgitation can result in shortness of breath, fatigue, heart arrhythmias, and even heart failure.

A common cause of mitral valve insufficiency is functional mitral valve regurgitation (FMR). FMR typically occurs when the left ventricle of the heart is enlarged, displacing the papillary muscles that support the valve leaflets of the mitral valve and stretching the annulus (valve opening). The resulting distortion to the annulus prevents the valve leaflets from coapting together to properly close the valve, allowing blood to flow backwards across the valve.

Mitral valve regurgitation is often treated by replacing the mitral valve with a replacement valve implant or by repairing the valve through an interventional procedure. One method for repairing the mitral valve is through annuloplasty. Annuloplasty is accomplished by delivering and implanting a ring or band in the annulus of the mitral valve to attempt to return the annulus to a functioning shape.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to devices for repairing tissue, such as a malfunctioning cardiac valve, including a regurgitant mitral valve. Some embodiments are directed to devices configured to provide repair of a regurgitant mitral valve without impeding the left ventricular outflow tract (LVOT) and/or aortic valve. For example, some embodiments are configured to enable, when deployed, proper coaptation of an anterior leaflet of a mitral valve against the device without imparting or transmitting radial forces in the septal direction which could impede, restrict, or hamper full functionality of the LVOT.

In some embodiments, a repair device includes a body having a perimeter that defines an upper side and a lower side, the perimeter having a posterior section and an anterior section. In some embodiments, the body is shaped so as to define an annular groove disposed along at least a portion of the posterior section, the annular groove being configured to receive tissue of a targeted anatomical location when the repair device is deployed at the targeted anatomical location. For example, in some implementations the annular groove is configured to receive posterior rim tissue of a targeted mitral valve.

In some embodiments, the repair device includes a first anchor and a second anchor, each anchor extending from the body in an anterior direction and configured to engage with tissue (e.g., commissure tissue of a targeted mitral valve) to prevent movement of the repair device from a targeted anatomical location when the repair device is deployed at the targeted anatomical location.

In some embodiments, the first and second anchors are substantially coplanar with the annular groove. In some embodiments, the body of the repair device is formed as a crescent-shape, with the concave side of the crescent shape defining the posterior section and the convex side of the crescent shape defining the anterior section. In some embodiments, the first anchor extends from a first intersection between the convex side and the concave side, and wherein the second anchor extends from a second intersection between the convex side and the concave side.

In some embodiments, the first anchor and/or second anchor are formed from one or more coiled or spiraled wire elements. In some embodiments, the first anchor and/or second anchor includes an upper section and a lower section (e.g., biased toward one another) to enable the gripping of tissue therebetween. In some embodiments, at least the body of the repair device includes a wire framework formed from a superelastic wire material. In some embodiments, the wire framework is incorporated with a cover or an insert.

In some embodiments, the repair device is radially outwardly biased along the posterior section and is not radially outwardly biased along the anterior section so as to prevent imparting forces to a septum of a heart when the repair device is deployed at the targeted mitral valve. In some embodiments, the body is configured in size and shape to enable an anterior leaflet of the targeted mitral valve to coapt and seal against the body.

Certain embodiments include a delivery device configured for delivery of a repair device. In some embodiments, a delivery device includes a delivery catheter having a proximal end and a distal end, a shaft disposed at least partially within the delivery catheter and configured to be translatable relative to the delivery catheter, and a repair device disposed at least partially within the delivery catheter distally from the shaft so that distal translation of the shaft and/or proximal withdrawal of the delivery catheter functions to unsheathe the repair device. In some embodiments, the repair device is housed within the delivery catheter in a collapsed configuration with at least one of the first or second anchor being positioned distally relative to the body to enable attachment of the distal anchor to targeted tissue (e.g., mitral valve commissure tissue) prior to unsheathing of the body from the delivery catheter.

Certain embodiments are directed to methods for manufacturing a repair device. In some embodiments, a method includes: forming a braid structure on a braiding mandrel; heat setting the braid structure on the braiding mandrel; removing the braid structure from the braiding mandrel; positioning the braid structure onto or into a shaping mandrel to shape the braid structure into a configuration having an annular groove and an extending section, the annular groove extending along a perimeter of a posterior section of the braid structure and the extending section extending away from the posterior section in an anterior direction; and heat setting the shaped braid structure.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

At least some of the embodiments described herein are directed to devices for repairing a malfunctioning cardiac valve, such as a regurgitant mitral valve. Some embodiments are directed to devices configured to provide repair of a regurgitant mitral valve without impeding the LVOT (including the aortic valve). For example, some embodiments are configured to enable, when deployed, proper coaptation of an anterior leaflet of a mitral valve without imparting or transmitting radial forces in the septal direction which could impede, restrict, or hamper full functionality of the LVOT.

Although many of the examples illustrated and described herein are directed to mitral valve regurgitation, and in particular mitral valve regurgitation related to FMR, it will be understood that the principles described herein may also be applied in other applications, such as mitral valve repair having non-FMR causes, repair of other heart valves, or use in other interventional procedures or treatment applications.

Figure 1A:
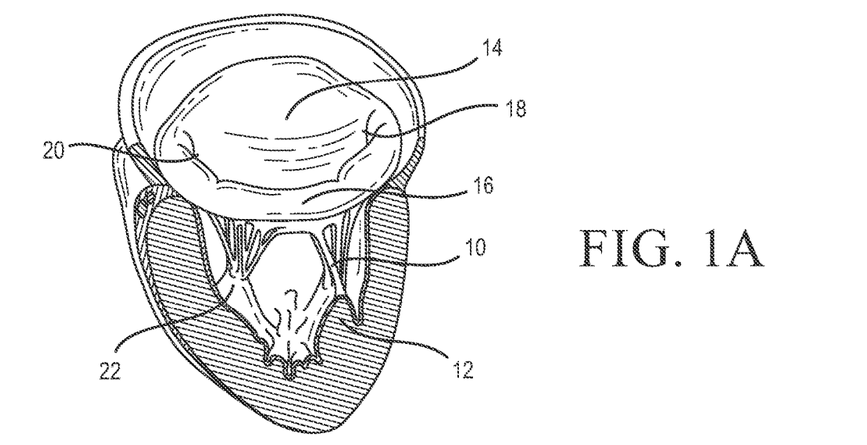
FIG. 1A illustrates a cross-sectional view of a heart with a normally functioning mitral valve.

FIG. 1A illustrates a cross-sectional view of a heart showing a normal, functional mitral valve in a closed position (during ventricular systole). The mitral valve includes an anterior leaflet 14 and a posterior leaflet 16, which are attached to papillary muscles 12 and 22 by chordae tendineae 10. Although the posterior leaflet 16 has a greater circumferential length, the anterior leaflet 14 extends over a greater portion of the valve opening. The anterior leaflet 14 and posterior leaflet 16 are joined at commissures 18 and 20 (posteromedial commissure 18 and anterolateral commissure 20). The commissures 18 and 20 define an area where the anterior leaflet 14 and the posterior leaflet 16 come together at the mitral valve annulus.

Figure 1B:
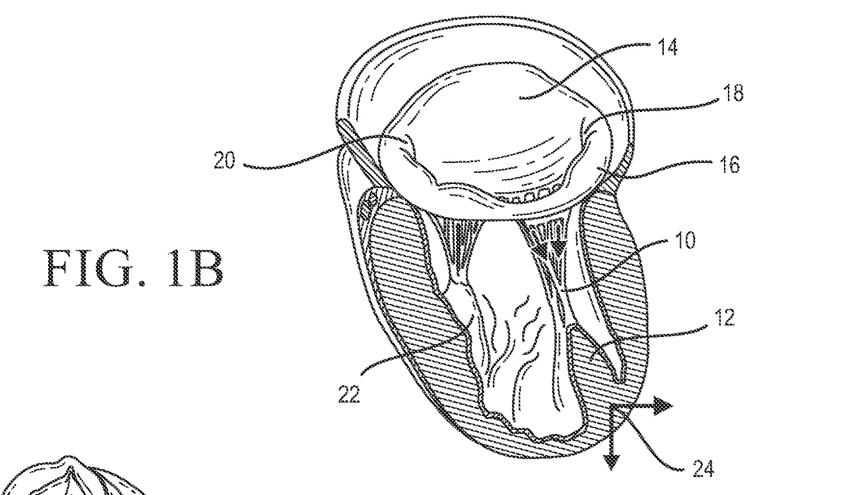
FIG. 1B illustrates a cross-sectional view of an enlarged heart resulting in functional mitral valve regurgitation.

FIG. 1B illustrates a cross-sectional view of a heart showing a regurgitant mitral valve as a result of FMR. As shown, the heart of FIG. 1B suffers from cardiomegaly ("enlarged heart"), which prevents adequate coaptation of the anterior leaflet 14 and posterior leaflet 16. As indicated by the arrows 24, the enlarged structure of the left ventricle pulls on the chordae tendineae 10 and prevents the leaflets 14 and 16 from properly coapting together. In the illustrated example, the posterior leaflet 16 is particularly displaced by the enlarged structure of the left ventricle. In many instances of FMR, the anterior leaflet 14 remains relatively mobile and able to contribute to sufficient leaflet coapting area, but the posterior leaflet 16 is constrained due to dilation of the annulus.

Figure 1C:
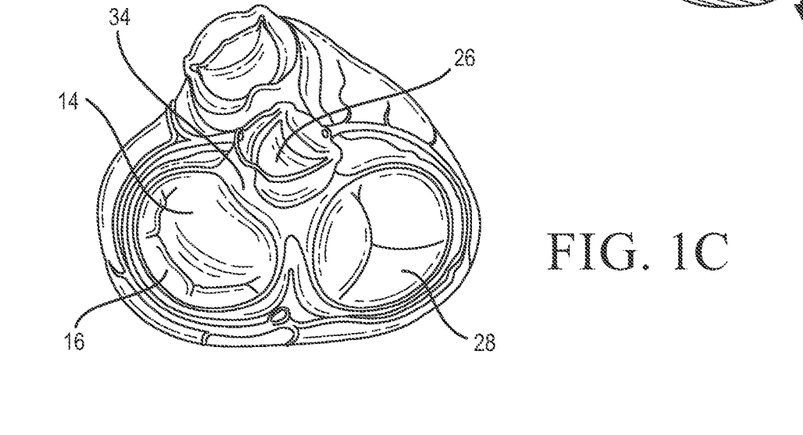
FIG. 1C illustrates a superior view of a heart showing the anterior leaflet 14 and posterior leaflet 16 of the mitral valve in the coapted position.

FIG. 1C illustrates a superior view of a heart showing the anterior leaflet 14 and posterior leaflet 16 of the mitral valve in the coapted position (during ventricular systole), along with the tricuspid valve 28 and open aortic valve 26. As shown, the relative positions of the aortic valve 26, the septum 34, and the mitral valve are such that radial forces from the anterior leaflet toward the septum 34 have the potential to impact the aortic valve 26 and/or other structures of the LVOT.

One regurgitant mitral valve treatment option involves implantation of a replacement mitral valve. However, replacement mitral valves are typically complex in construction and also involve complexities in delivery and deployment. For example, mitral valve replacement includes difficulties related to achieving anatomical conformity to a misshaped annulus, durability of artificial leaflets, and forming a tolerable septal crossing profile (e.g., less than about 29 Fr for acceptable femoral delivery and transeptal crossing to the left atrium without requiring subsequent septal repair). Further, the implantation of a replacement valve often requires removal or alteration of the leaflets and/or other associated structures. The inability to preserve these structures limits subsequent treatment options.

Another treatment option is annuloplasty. However, a typical annuloplasty implant, once deployed, imparts and/or allows transmittal of radial forces to the septum, which can result in compromised LVOT function. Accordingly, in many instances an annuloplasty implant may function to reduce regurgitation, but at the same time may cause or aggravate other detrimental conditions within the patient's heart.

One or more of the embodiments described herein are configured to enable repair of a regurgitant mitral valve while also avoiding one or more of the foregoing limitations of a valve replacement or typical annuloplasty procedure. For example, some embodiments are configured to enable repair of a regurgitant mitral valve without imparting or transmitting radial forces to the septum. Further, some embodiments are configured to reduce or eliminate mitral valve regurgitation while preserving leaflet and/or other valvular structures, which may be beneficial in subsequent removal, repair, or replacement procedures, or in preserving a greater number of future treatment options, for example.

Figure 2A:
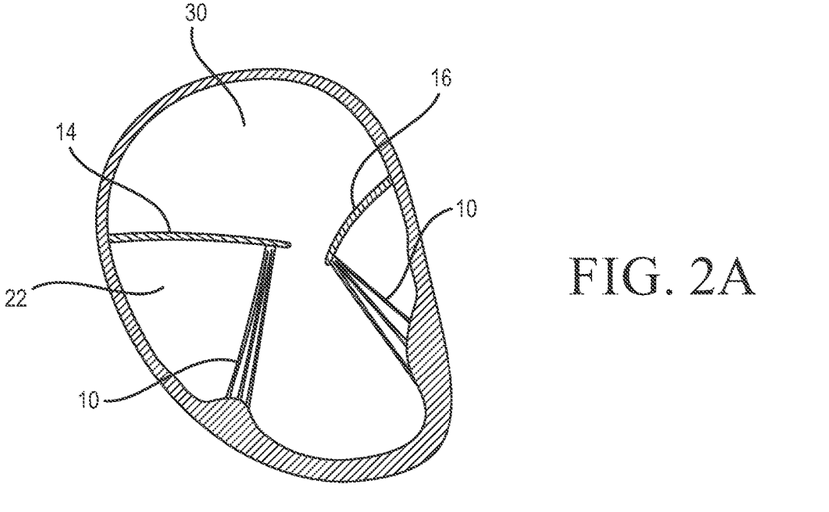
FIG. 2A illustrates a cross-sectional view of a heart with a regurgitant mitral valve prior to deployment of a repair device.
Figure 2B:
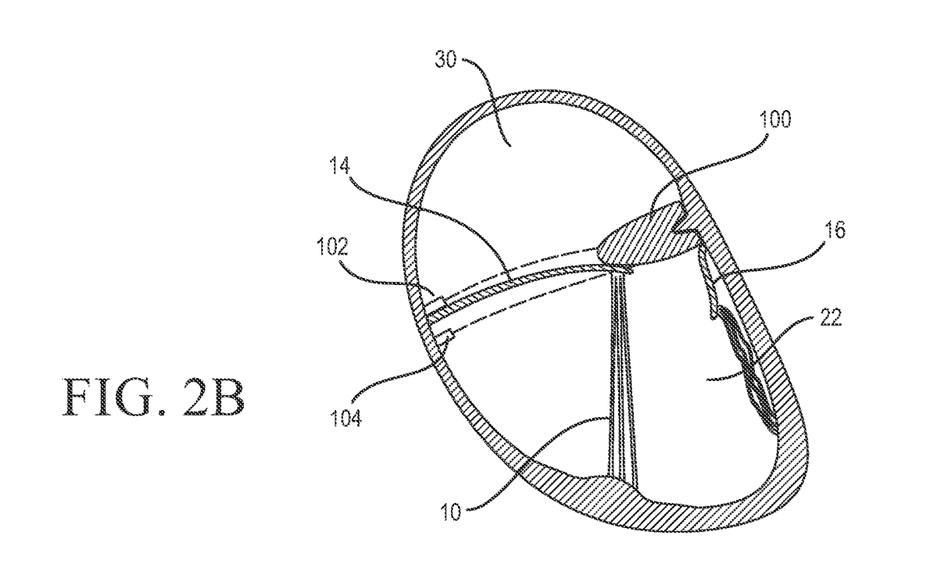
FIG. 2B illustrates a cross-sectional view of the heart of FIG. 2A after deployment of a repair device.

FIGS. 2A and 2B illustrate additional cross-sectional views of a heart with FMR, with FIG. 2A showing the heart before deployment of a repair device 100 and FIG. 2B showing the heart after deployment of the repair device 100. As shown in FIG. 2A, the posterior leaflet 16 is constrained by corresponding chordae tendineae 10 and is unable to properly coapt with the anterior leaflet 14, allowing blood to pass backward from the left ventricle 22 to the left atrium 30. FIG. 2B illustrates the repair device 100 in a deployed position on the posterior rim of the mitral valve annulus.

In some embodiments, the repair device 100 is configured to function as a static or rigid posterior leaflet, allowing the relatively more mobile anterior leaflet 14 to provide the dynamic functionality of the mitral valve. For example, because the posterior leaflet 16 extends a shorter distance across the valve (i.e., from the annulus to the leaflet margin) than the anterior leaflet 14, the implant profile of the repair device 100 may not overly restrict flow through the valve, even if the repair device 100 is configured as static or rigid. In alternative embodiments, the repair device 100 is configured with a degree of flexibility to enable dynamic movement that more closely resembles natural movement of the posterior leaflet 16.

As shown, the repair device 100 is positioned to extend across the mitral valve toward the anterior leaflet 14 a distance sufficient to allow the anterior leaflet 14 to close against the repair device 100 and prevent regurgitation during ventricular systole. As explained in more detail below, the repair device 100 includes anchors 102 and 104 which, when the repair device is deployed, are positioned within corresponding commissures of the mitral valve. In some embodiments, the anchors 102 and 104 are positioned so as to stabilize and support the repair device in the deployed position while minimizing or preventing septal directed forces of the repair device 100.

Figure 3A:
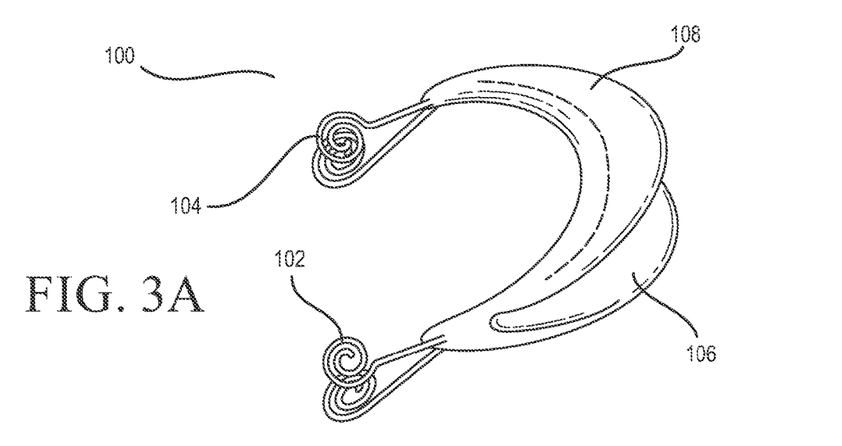
FIGS. 3A-3C illustrate various views of an exemplary embodiment of a repair device.
Figure 3B:
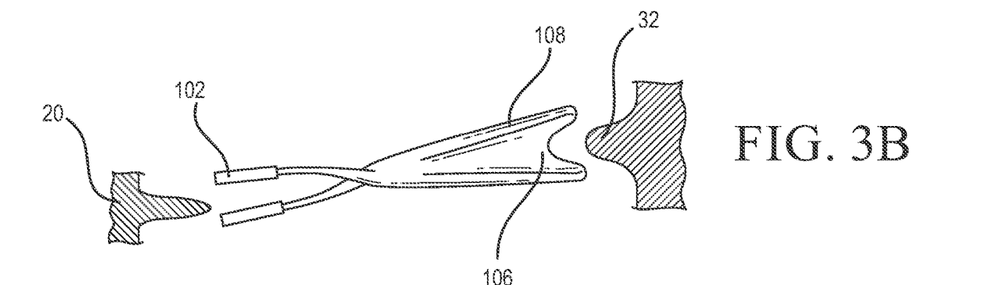
Figure 3C:
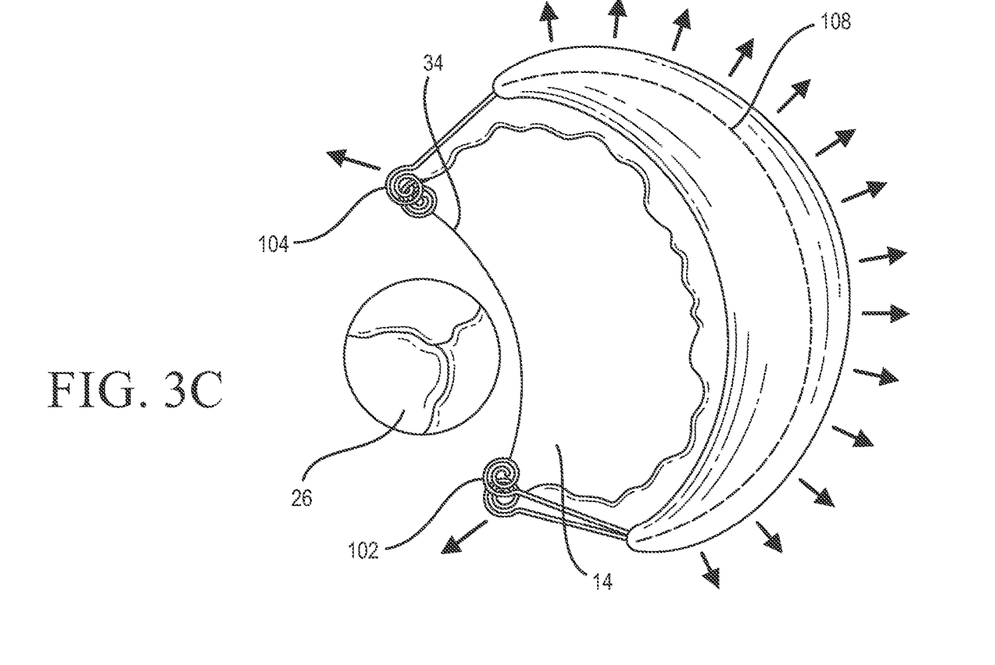

FIGS. 3A-3C illustrate various views of the exemplary repair device 100. FIG. 3A illustrates an isometric view of the repair device 100, showing a crescent-shaped body 108 of the device and the anchors 102 and 104 extending from the body 108 in an anterior direction. In the illustrated embodiment, the body 108 is formed so as to define a groove 106 disposed along a posterior section of the body 108. As shown, the repair device 100 is structured so that when deployed, the repair device 100 does not need to conform or attach to the entirety of the annular circumference of the mitral valve annulus. Rather, as best shown in the side view of FIG. 3B, the illustrated repair device 100 is able to be deployed along the posterior rim 32 of the annulus.

In the illustrated embodiment, the groove 106 allows the repair device 100 to be deployed and registered against the posterior rim 32, while the anchor 102 allows attachment to the commissure 20 (and the opposite anchor allows attachment to the opposite commissure). In some embodiments, the groove 106 and/or anchors 102 and 104 operate to prevent upward or downward movement of the device 100 into the atrium or ventricle once it has been deployed. For example, as shown in the illustrated embodiment, the anchors 102 and 104 and/or the groove 106 provide both atrial-side and ventricular-side engagement of annular tissue to prevent atrial and ventricular migration of the device. In some embodiments, the groove 106 also reduces or prevents the occurrence of paravalvular leakage (e.g., leakage between the repair device and the posterior rim) during ventricular systole.

FIG. 3C illustrates a superior view of the repair device 100 in a deployed position showing that the anterior leaflet 14 is able to close against the body 108 of the repair device. The anchors 102 and 104 are positioned at the commissures (not shown). As illustrated, the repair device 100 is configured so that when deployed, forces are imparted radially against the posterior rim of the annulus, but not radially against the septum 34. For example, when deployed, the repair device 100 will be outwardly radially biased along the posterior section; however, the structure of the repair device 100 prevents any outward radial forces extending from the anterior section of the device 100. This configuration and distribution of forces beneficially minimizes or avoids imparting pressure across the septum 34 and to the aortic valve 26 or other structures of the LVOT. In addition, in at least some implementations, the illustrated configuration minimizes or eliminates any detrimental effect to the functioning of the anterior leaflet 14.

In some embodiments, the anchors 102 and 104 and/or other components of a repair device are formed from a superelastic material, such as a nickel-titanium alloy. When deployed, the anchors 102 and 104 are preferably configured to flex to reduce tissue damage and/or necrosis. In some embodiments, the anchors 102 and 104 and/or other components of a repair device are treated to reduce the likelihood of thrombus formation and/or encourage tissue ingrowth and endothelialization. For example, one or more components of a repair device may be coated with a mesh covering (e.g., a polyester woven sock) or other tissue growth promoter to encourage tissue ingrowth. Additionally, or alternatively, the anchors 102 and 104 and/or other components of a repair device may be coated with a biocompatible film and/or other surface treatment.

In some embodiments, the anchors 102 and 104 are formed from a superelastic nickel-titanium alloy or other superelastic material, and the remainder of the repair device is formed from a biocompatible polymer, such as one or more of an ultra-high molecular weight polyethylene (UHMWPE), polyether ether ketone (PEEK), polyester, or a flexible biogel. Preferably, at least the body 108 of the repair device 100 is formed from a material that minimizes metallic interference with magnetic resonance imaging (MRI), computed tomography (CT) scanning, fluoroscopy, or other imaging technique. In some embodiments, one or more struts are passed through the body 108 to provide structure to the repair device 100. For example, a wire framework may support a cover and/or insert to form the device 100. In some embodiments, superelastic wire material utilized to form one or more of the anchors may pass through the body 108 of the repair device to form a wire framework that may be covered or coupled with an insert formed from a separate polymer material or other suitable biocompatible material.

FIGS. 4A-4D illustrate various configurations of an anchor 202 that may be utilized in one or more of the repair device embodiments described herein for attachment to a commissure 20. Preferred anchor configurations include curved and/or castellated structures to increase surface contact and reduce point pressure on tissue once deployed. In the illustrated embodiments, the anchors 202 include upper and lower (e.g., atrial and ventricular) sections for engaging opposite sides of a commissure 20 when deployed. In some embodiments, the opposite sides are configured to be biased toward one another to provide a holding force for engaging a commissure when deployed.

Figure 4A:
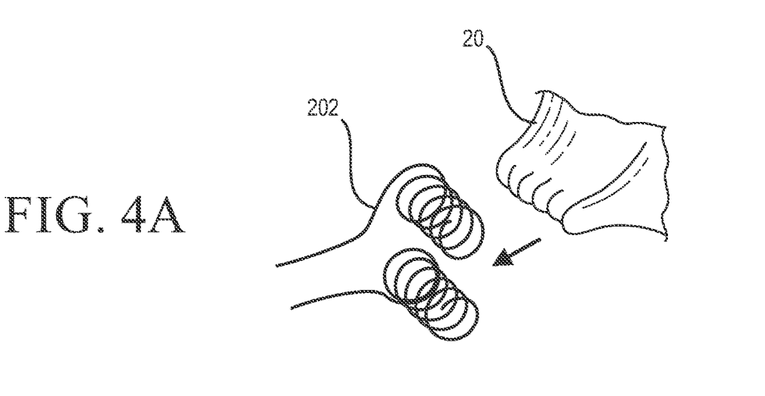
FIGS. 4A-4D illustrate various exemplary configurations of an anchor of a repair device.
Figure 4B:
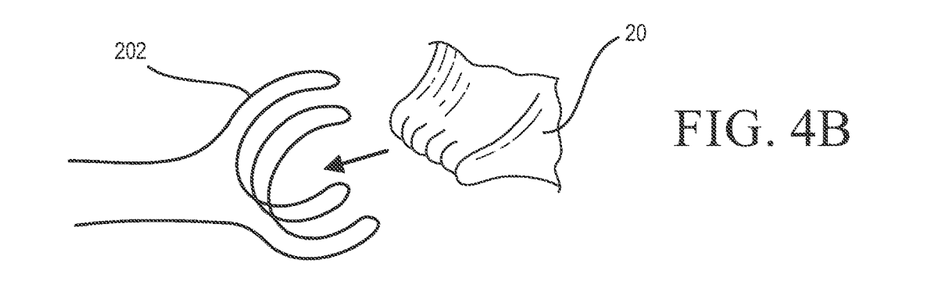
Figure 4C:
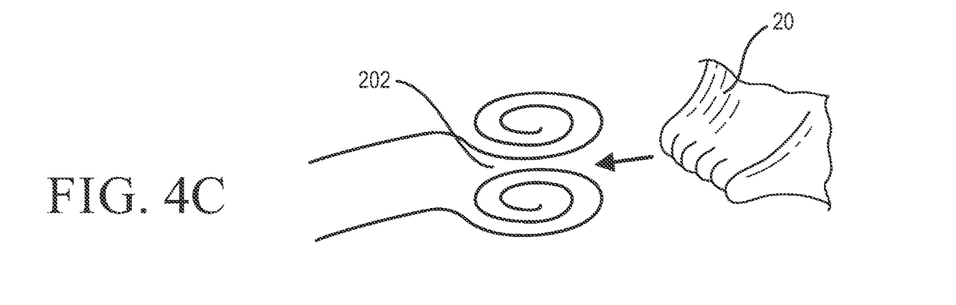
Figure 4D:
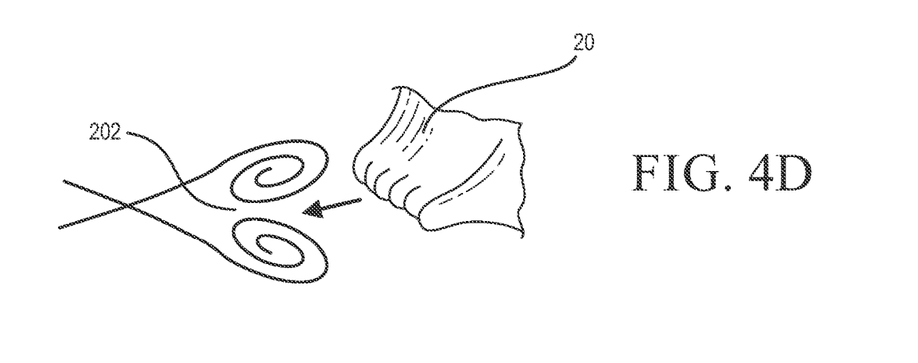

The illustrated anchors 202 are formed as wires shaped to provide an anchor configuration. For example, wires (e.g., nickel-titanium alloy wires) can be shaped to form one or more of circles, spirals, loops, and the like. As shown, a pair of opposing wires may be utilized to form upper and lower (e.g., atrial and ventricular) sections. In some embodiments, one or more wires may be structured to form an arrangement of vertically oriented coils, as shown in FIG. 4A. In some embodiments, one or more wires may be arranged to form a crescent-shaped structure, as shown in FIG. 4B. In some embodiments, one or more wires may be arranged to form a horizontally oriented spiral, as shown in FIGS. 4C and 4D.

In some embodiments, one or more anchors include one or more barbs, hooks, tines, or other fixing structures configured to enhance fixation of the anchor to the commissure tissue when deployed and to increase resistance to dislodging of the anchor caused by hemodynamic forces across the valve. Additionally, or alternatively, one or more anchors may include an enhanced surface area or roughened surface texture adapted to increase tissue grip and resistance to dislodging.

Figures 5, 6A:
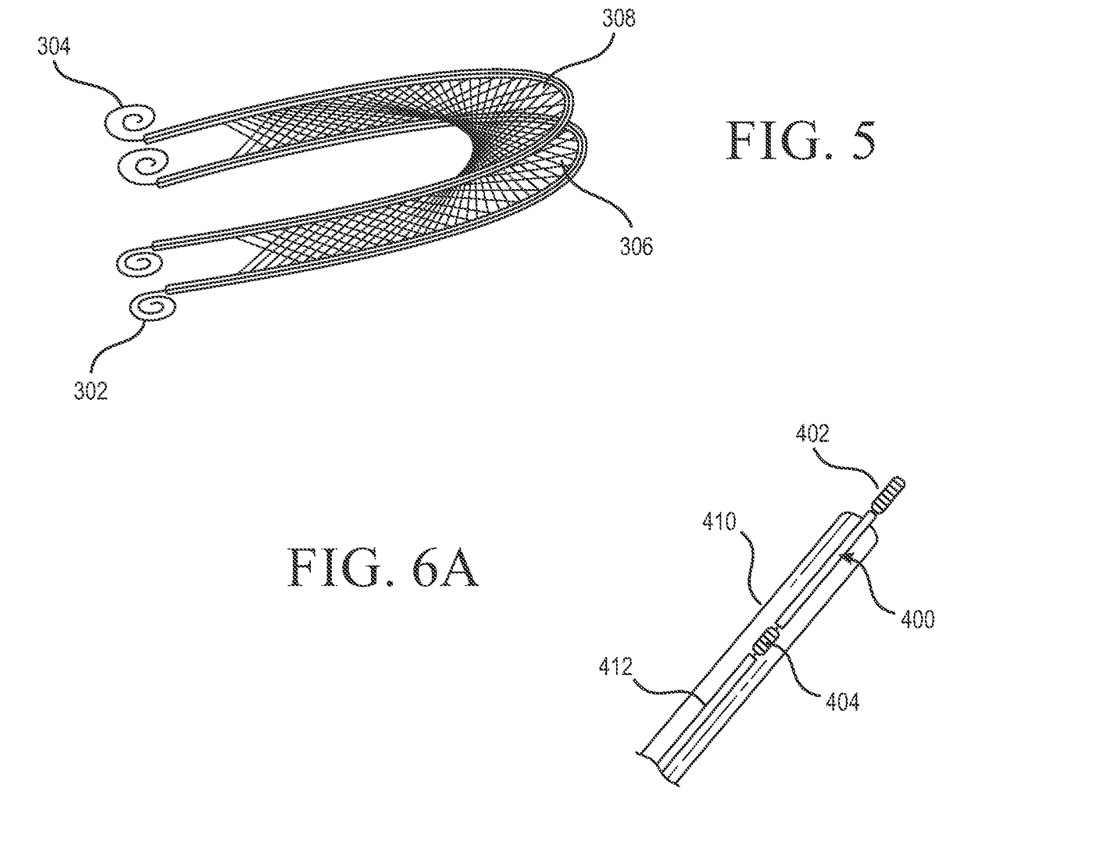
FIG. 5 illustrates an alternative embodiment of a repair device.
FIGS. 6A-6B illustrate an exemplary embodiment of a delivery system configured for delivering a repair device to a targeted anatomical area within a patient's body.

FIG. 5 illustrates an alternative embodiment of a repair device including a body 308 shaped so as to define a posterior facing groove 308 and anchors 302 and 304 extending in an anterior direction from the body 308. The illustrated embodiment is configured as a set of opposing crescent-shaped wires joined by a woven and/or mesh covering material or webbing extending between the opposing wires. When deployed, a first wire would be disposed on the atrial side of the posterior rim of the annulus while a second wire would be disposed on the ventricular side of the posterior rim of the annulus, with the covering material extending across and abutting against the posterior rim. In some embodiments, this configuration beneficially provides one or more of effective tissue ingrowth, minimized posterior dilation of the repaired valve, and low-profile construction which enables non-invasive delivery (e.g., transfemoral). In some embodiments, the shape may be delivered in a closed or collapsed configuration which opens to an open or expanded configuration during deployment. Exemplary methods and systems related to delivery and deployment of a repair device are described in more detail below.

One or more components of the illustrated embodiment may have variable thickness to provide desired structure and/or strength. For example, the anchor regions 302 and 304 may be provided with more structure and strength relative to the webbing. Additionally, or alternatively, variable gauges of wire may be used in a forming process so as to manage the profile (collapsed and/or expanded) of the repair device while imparting strength where needed (e.g., the anchor and/or annulus regions of the device). The illustrated embodiment is shown as a shaped wireframe structure. In other embodiments, a repair device may have a half-stent construction, such as formed by cutting (e.g., laser cutting) stent tubing to form the repair device shape as illustrated.

The sections of the repair device which are contacted against the posterior rim of the annulus when the device is deployed (e.g., the sections within the groove 306) are preferably porous and/or surface treated so as to encourage tissue ingrowth. The surfaces contacting the anterior leaflet and functioning to obstruct regurgitation (e.g., the non-groove sections of the body 308) are preferably non-porous and/or smooth to enable obstruction of regurgitant flow while minimizing effects on functioning of the anterior leaflet.

An alternative embodiment of a repair device includes one or more components formed from a porous polymer (e.g., formed from a foam-like polymer material). For example, such a repair device may be delivered to a targeted valve in a compressed and low profile configuration, and then upon deployment and saturation with blood, the repair device opens to an expanded configuration. Additionally, or alternatively, a repair device may include one or more Tillable chambers that may be filled, for example, with saline, a biogel, or a curable resin. By way of example, a repair device may be delivered in a compressed configuration. During or after deployment, the one or more chambers may then be filled to at least partially open the device toward an expanded configuration. Such embodiments are preferably formed from a material that resists hemodynamic flow through the material (e.g., during ventricular systole) and allows coaptation with the anterior leaflet.

In some embodiments, a repair device includes a body having a solid structure. In alternative embodiments, a repair device includes a body formed as a wireframe structure that may be covered by or integrated with a covering. Additional examples of repair device structures are described in more detail below.

Figure 6B:
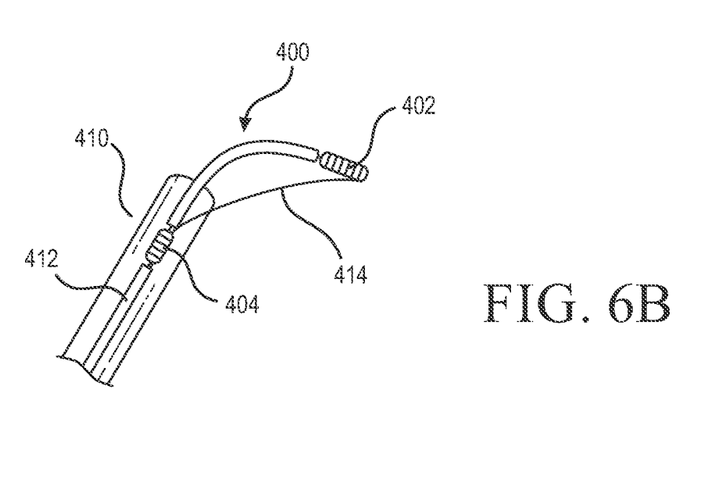

FIGS. 6A and 6B illustrate an example repair device delivery system including a repair device 400 with anchors 402 and 404, the repair device 400 being housed within a delivery catheter 410. The repair device 400 may represent any of the repair device embodiments described herein. The illustrated embodiment includes a shaft 412 which may be abut or be coupled to a proximal end of the repair device 400 (e.g., at anchor 404) and housed within the delivery catheter 410 along with the repair device 400. The shaft 412 and delivery catheter 410 are translatable relative to one another such that the repair device 400 may be unsheathed from the distal end of the delivery catheter by distal pushing of the shaft 412 relative to the delivery catheter 410 and/or proximal withdrawal of the delivery catheter 410 relative to the shaft 412.

In the illustrated embodiment, the anchor 402 is positioned at the distal end of the repair device 400. In one exemplary implementation, the repair device 400 may be partially unsheathed from the delivery catheter 410 so as to expose the distal anchor 402, resulting in the configuration shown in FIG. 6A. the distal anchor 402 may be directed to a commissure of the targeted valve (e.g., the posteromedial commissure) to engage with the commissure. The repair device 400 may then be further unsheathed from the delivery catheter 410 so as to expose the body of the repair device 400 for engagement with the posterior rim of the mitral valve. In preferred embodiments, the repair device 400 has sufficient rigidity to remain secured against the annulus while the remainder of the repair device 400 is unsheathed from the delivery catheter 410.

Further unsheathing reveals the proximal anchor 404, which is directed to the remaining commissure (e.g., the anterolateral commissure) to engage with the commissure. In some embodiments, one or more of the anchors 402 and 404 are formed from a shape memory material such that they conform to a three-dimensional shape to capture and/or engage with the respective commissures upon being unsheathed from the delivery catheter 410.

In some embodiments, the length of the repair device is sized prior to delivery and deployment of the device. For example, a repair device may be sized for a particular patient based on imaging or other factors. In other embodiments, the size of the repair device is adjustable. For example, one or more of the anchors may be translatable along at least a portion of the length of the repair device in a ratcheting or "zip-tie" fashion.

FIG. 6B illustrates a configuration of the repair device delivery system including a control wire 414 attached at or near the distal end of the repair device 400 and passing proximally through the delivery catheter 410 to a control handle (not shown). Tensioning of the control wire 414 enables steering of the distal end of the repair device 400 toward its anatomical target (e.g., one of the commissures). The control wire 414 may be formed as a braided polymer or monofilament, for example. One or more control wires may be routed internally within the delivery catheter 410, such as within grooves or lumens of the delivery catheter 410, such that when tensioned, the one or more control wires do not consume outboard space and/or interfere with anatomic structures.

Figure 7A:
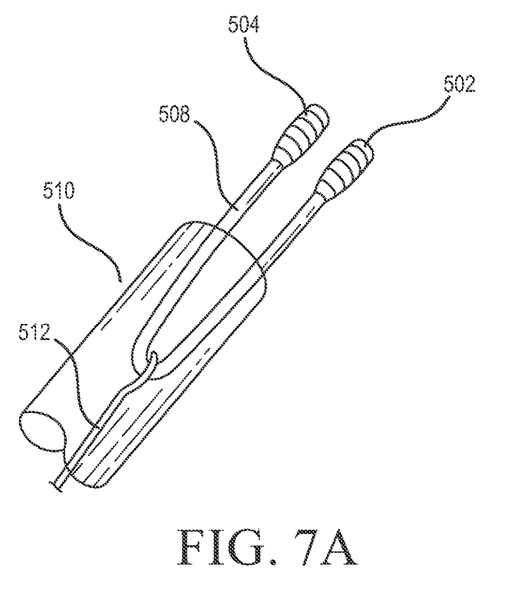
FIGS. 7A-7C illustrate an alternative embodiment of a delivery system configured for delivering a repair device to a targeted anatomical area within a patient's body.
Figure 7B:
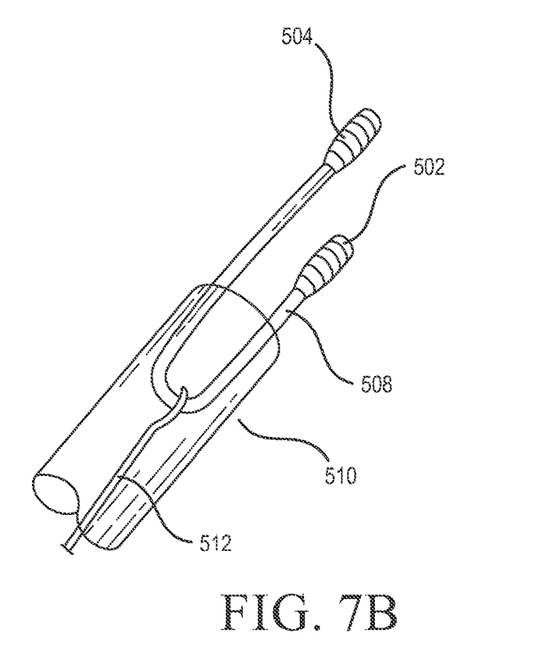
Figure 7C:
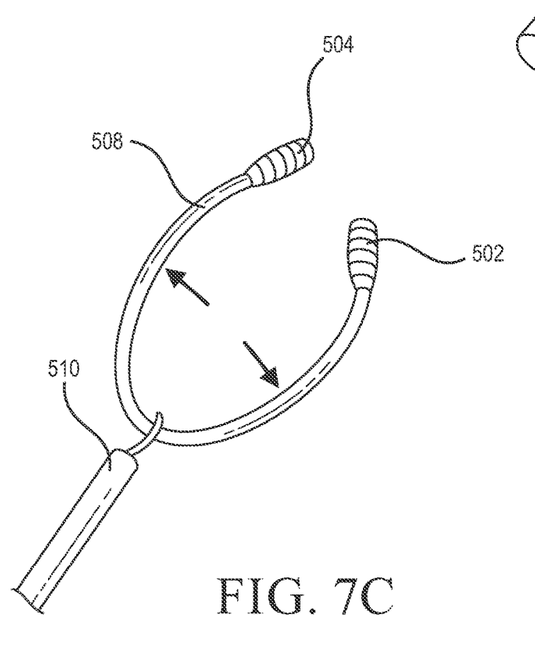

FIGS. 7A-7C illustrate another embodiment of a repair device delivery system for delivery of a repair device having a body 508 and anchors 502 and 504. The illustrated embodiment includes a delivery catheter 510 and a rod 512 disposed radially within the delivery catheter 510 and configured to be translatable relative to the delivery catheter 512. As shown, the rod 512 is coupled to the body 508 of the repair device so as to enable the repair device to be unsheathed from the delivery catheter 510 by pushing the rod 512 distally relative to the delivery catheter 510 and/or withdrawing the delivery catheter 510 proximally relative to the rod 512. In the illustrated embodiment, the rod 512 includes a hooked end for engaging around the body 508 of the repair device. In other embodiments, a rod may omit a hook so as to function as a push structure, or may be detachably adhered, magnetically coupled, and/or mechanically fastened to the repair device, for example.

The configuration shown in FIG. 7A positions the anchors 502 and 504 substantially equally from the rod 512. FIG. 7B shows an alternative configuration where the anchors 502 and 504 are positioned in an offset fashion, with the anchor 504 being positioned further distally from the rod 512 than the anchor 502. Such an offset configuration may enable a lower overall profile for the repair device when positioned within the delivery catheter 510. FIG. 7C illustrates deployment of the repair device from the delivery catheter 510. In the illustrated embodiment, the body 508 of the repair device moves toward an expanded configuration when unsheathed from the delivery catheter 510. The body 508 and/or other components of the repair device may be formed from a shape-memory material that provides such functionality to the repair device.

The embodiment shown in FIGS. 7A-7C is configured with the anchors 502 and 504 of the repair device positioned distally relative to the body 508, such that the anchors 502 and 504 are unsheathed before the remainder of the body 508 of the repair device. Such an embodiment beneficially allows the anchors 502 and 504 to be attached to respective commissures prior to fully unsheathing the body 508 of the repair device and unfolding or expanding of the repair device. However, in other embodiments, a repair device may be oriented within a delivery catheter with anchors positioned proximally relative to the body of the repair device, such that at least a portion of the body is unsheathed from the delivery catheter prior to the anchors being unsheathed.

The embodiment shown in FIGS. 7A-7C beneficially enables delivery of a repair device from a positon or orientation that is transverse to the mitral valve plane. For example, transeptal delivery of the delivery catheter 510 may result in the distal end of the delivery catheter being oriented transverse to the mitral valve plane. Steering and positioning of the repair device (e.g., elevation, axial rotation, pitch) may be adjusted by manipulating the rod 512. After lodging the anchors 502 and 504 in their respective commissures, manipulation of the rod 512 relative to the delivery catheter 510 enables the body 508 of the repair device to be properly positioned/oriented for deployment against the posterior annular rim of the mitral valve.

Other delivery methods may also be utilized. For example, a repair device may be delivered surgically or transapically. In one example of a transapical approach, a repair device is introduced through the apex of the left ventricle wall and brought to the valve plane before deployment.

Embodiments described herein may be formed with a lower profile and lower bending stiffness than a conventional valve replacement device. The relatively small profile and low bending stiffness provide beneficial utility as compared to such conventional valve replacement procedures. Reductions in complications related to arrhythmias and/or LVOT obstruction may be provided by the devices, systems, and methods described herein. Further, such devices are relatively easy to orient and properly position.

In some embodiments, particularly those intended for transcatheter delivery, one or more radiopaque markers may be included at various locations of the device. Such marker may be placed on the device to identify orientation details with respect to how the device is positioned in the mitral valve. In one embodiment, a marker is placed at a mid-septum section of the device to aid the user in registering device orientation.

FIGS. 8 through 12D illustrate various process steps directed to the manufacture of a repair device as described herein. One or more of the illustrated and described steps may be utilized to manufacture, at least in part, one or more of the repair device embodiments described herein. In one exemplary method, a repair device is manufactured by: forming a braid structure on a braiding mandrel; heat setting the braid structure on the braiding mandrel; positioning the braid structure onto or into a shaping mandrel to shape the braid structure into a configuration having an annular groove and an extending section, wherein the annular groove extends along a perimeter of a posterior section of the braid structure and the extending section extends away from the posterior section in an anterior direction such that the annular groove is configured to accommodate a posterior annular rim of a mitral valve and the extending section is configured to accommodate coaptation of an anterior leaflet against the extending section; and heat setting the braid structure. Some embodiments may further include one or more of laser welding sections of the structure(s) together, passivating and/or electro-polishing the finished braid structures, attaching an insert and/or cover to the braid structure, and loading the braid structure into a delivery catheter to form a repair device delivery system.

Figure 8:
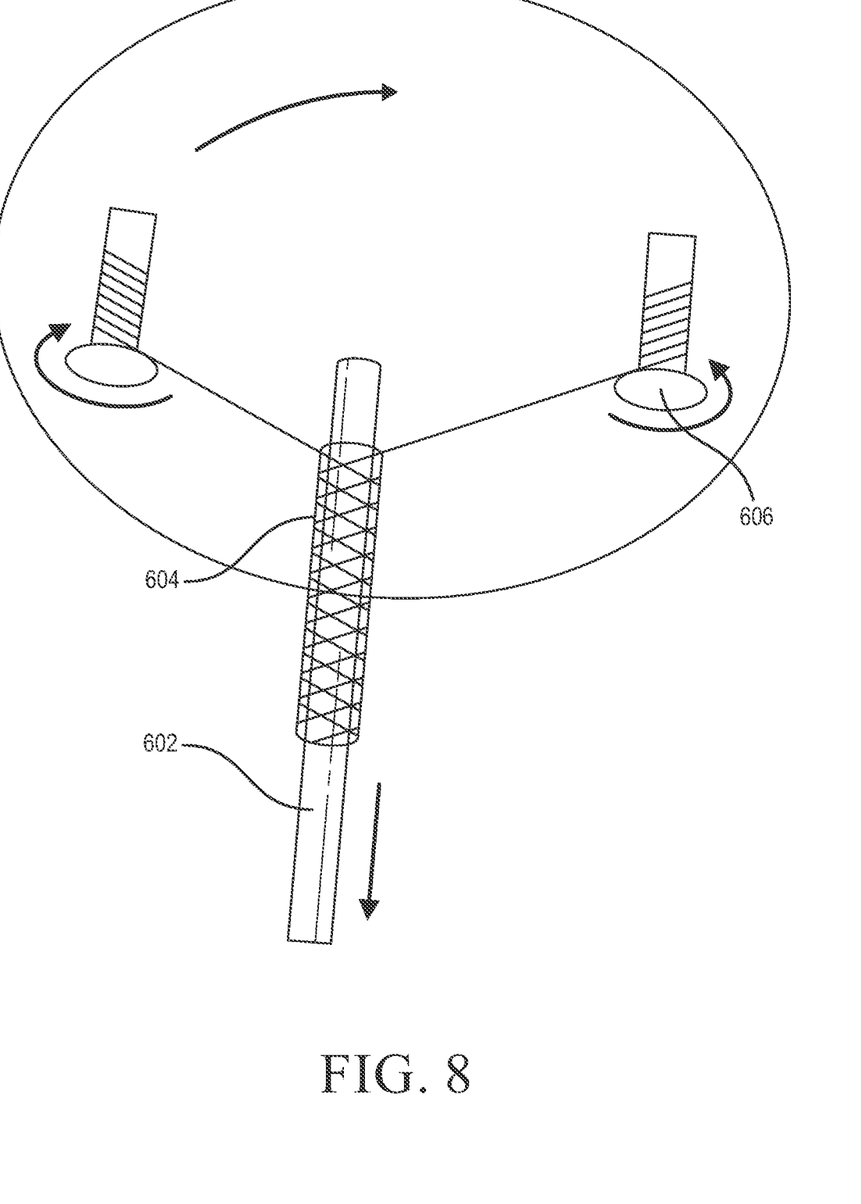
FIG. 8 illustrates the formation of a braid structure on a mandrel as part of an exemplary process for manufacturing a repair device.

FIG. 8 illustrates a manufacturing device that may be used as at least part of a process for manufacturing a repair device, such as one or more of the repair device embodiments described herein. In the illustrated embodiment, a braid structure 604 is formed by wrapping wire around a mandrel 602 as the mandrel 602 is displaced relative to one or more spool components 606. The illustrated mandrel 602 has a cylindrical shape. Other embodiments may include mandrels having alternative shapes, such as tapering cylinders, tapering or non-tapering ovoid cross-sectional shapes, tapering or non-tapering polygonal cross-sectional shapes, and shapes having a wing-like cross-section matching the geometry of a posterior leaflet, for example. Wires used to form the braid structure 604 may be formed from a super-elastic material, such as a suitable nickel titanium alloy. Other embodiments may utilize wire formed from other metals, alloys, or polymers.

Wires used to construct various sections of the device may have different cross sections to reduce the overall profile of the device when collapsed into the delivery catheter and/or to provide strength to the anchoring features. One or more wires may also include undulations and/or other non-linear features to improve intra-strut interactions, strength, and/or to reduce profile. Various manufacturing steps are described in more detail below.

In some embodiments, after a braid structure 604 has been formed, the free ends are back-braided, welded, adhered, or otherwise incorporated into the body of the braid structure 604. The braid structure 604 may then be heat set (e.g., at about 500 to 550 degrees C. for about 15-20 minutes) while still being held on the mandrel 602. For example, in some embodiments, the braid structure 604 is formed from a shape memory material, such as a nickel titanium alloy having shape memory properties.

Figure 9A:
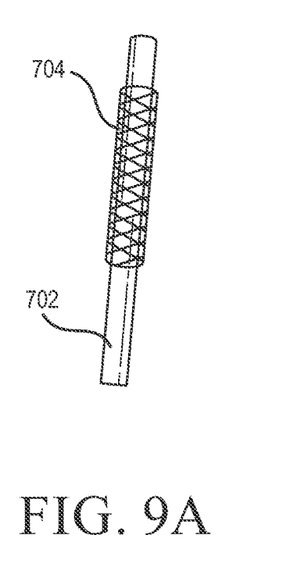
FIGS. 9A-9C illustrate various exemplary mandrel shapes.
Figure 9B:
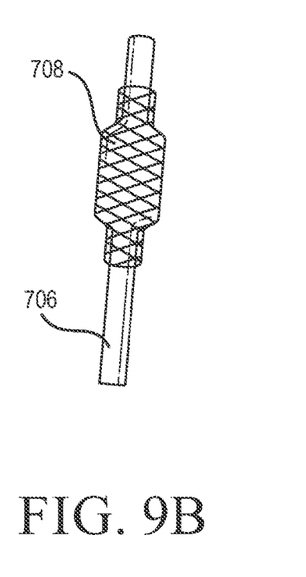
Figure 9C:
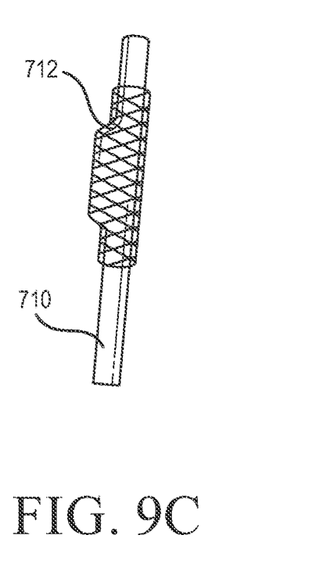
Figure 10A:
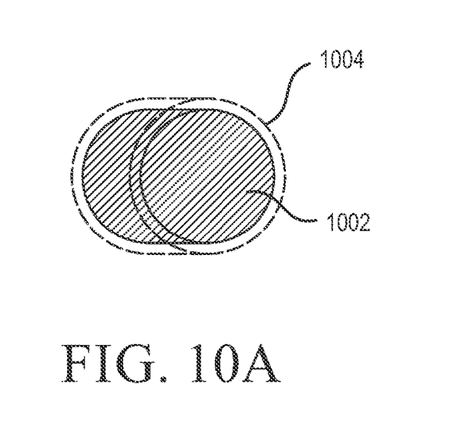
FIGS. 10A-10D illustrate cross-sectional views of various exemplary braid structure shapes formed on corresponding mandrels.
Figure 10B:
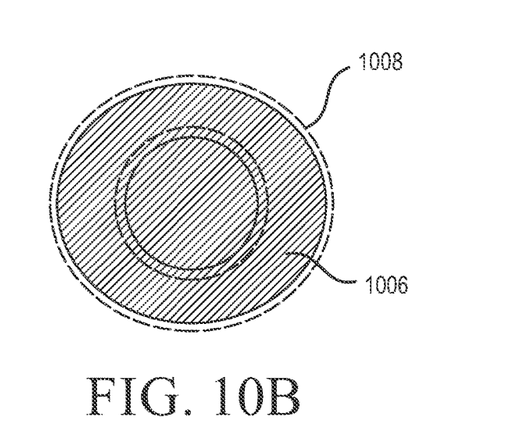
Figure 10C:
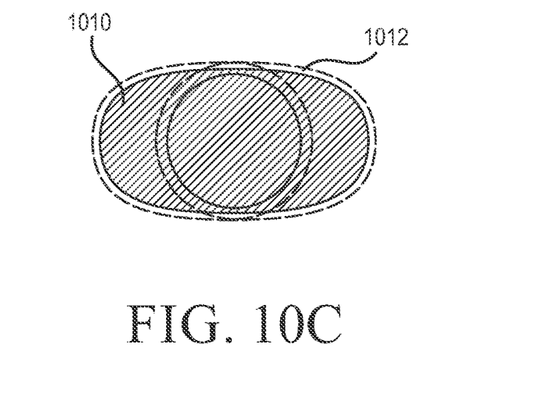
Figure 10D:
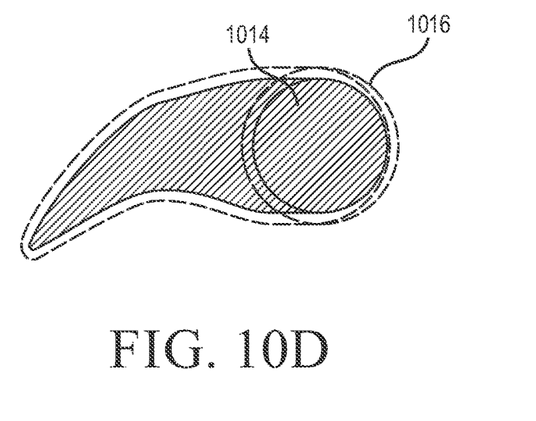

FIGS. 9A-9C illustrate various mandrels 702, 706, and 710 having different shapes to form different respective braid structures 704, 708, and 712. FIGS. 10A-10D illustrate cross-sectional views of various mandrels 1002, 1006, 1010, and 1014 having different shapes to form different respective braid structures 1004, 1008, 1012, and 1016. For example, FIG. 10A illustrates a mandrel 1002 having an eccentric tubular cross-sectional shape, FIG. 10B illustrates a mandrel 1006 having a coaxially tapered tubular shape, FIG. 10C illustrates a mandrel 1010 having a cross-sectional shape that transitions from circular to ovoid, and FIG. 10D illustrates a mandrel 1014 having a wing-like cross-sectional shape similar to a posterior leaflet profile shape.

Figure 11A:
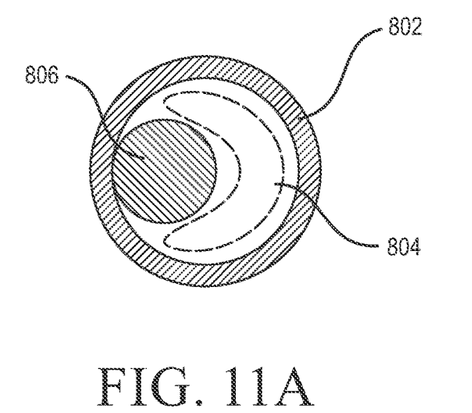
FIGS. 11A and 11B illustrate cross-sectional views of shaping mandrels configured for further shaping of braid structures into shapes suitable for providing functionality as repair devices.
Figure 11B:
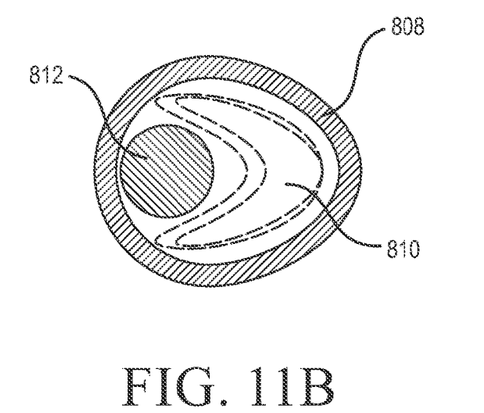

In some embodiments, after heat setting of a braid structure onto a braiding mandrel, the braid structure is removed from the mandrel (e.g., using split tubes for some part geometries, as needed) and placed onto or into a shaping mandrel for further shaping of the braid structure. FIGS. 11A and 11B illustrate, in cross-sectional view, placement of braid structures 804 and 810 into shaping mandrels 802 and 808, respectively. In the illustrated embodiment, the shaping mandrels 802 and 808 are formed as hollow cavity mandrels to constrain and shape the outer periphery sections of the respective braid structures 804 and 810. The illustrated shaping mandrels 802 and 808 also include respective shaping rods 806 and 812 for further defining and shaping of the periphery sections of the braid structures 804 and 810.

The illustrated embodiments form braid structures 804 and 810 having a generally V-shaped cross section for providing an annular groove structure and an extending section. For example, one or more shaping rods may be utilized to form an annular groove shape enabling engagement of a resulting repair device with commissure tissue and/or posterior annular rim tissue upon deployment of the repair device. In addition, an extending section enables a resulting repair device to provide a coapting surface against which an anterior leaflet may close once the repair device has been deployed in a targeted mitral valve.

The embodiment shown in FIG. 11A has a non-tapering profile, while the embodiment shown in FIG. 11B has a tapering profile. After shaping of a braid structure in a shaping mandrel, the braid structure may be subjected to heat setting to set the final shape of the braid structure. The heat setting parameters may be as described above (e.g., about 500 to 550 degrees C. for about 15 to 20 minutes for nickel-titanium alloy based embodiments) or other suitable combination of temperature and time to provide desired shape setting of the shape-memory material of the braid structure (e.g. a particular time and temperature combination suitable for the particular type of shape memory material used).

Figure 12A:
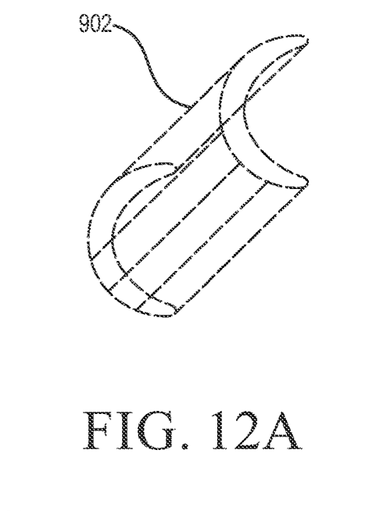
FIGS. 12A-12D illustrate various views of exemplary braid or wireframe structures formed using respective shaping mandrels.
Figure 12B:
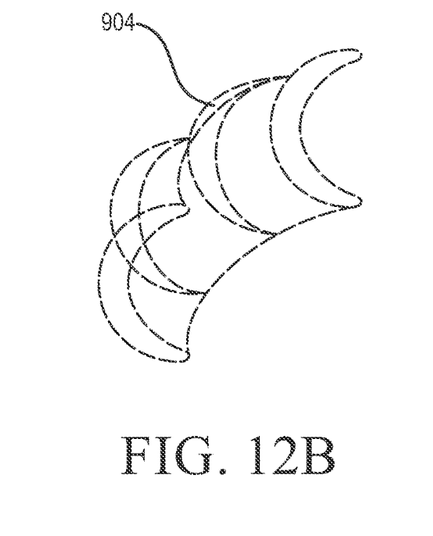
Figure 12C:
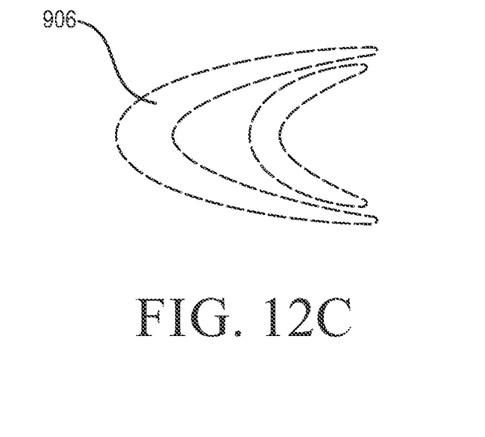
Figure 12D:
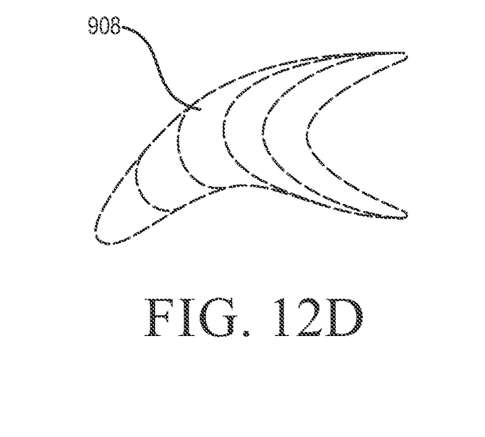

FIGS. 12A-12D illustrate views of various braid structures 902, 904, 906, and 908 that may be formed using a shaping mandrel as described by the foregoing. For example, FIG. 12A illustrates a braid structure 902 having a crescent-shaped cross section, FIG. 12B illustrates a braid structure 904 having a crescent-shaped cross section and an axially curved profile, FIG. 12C illustrates a braid structure 906 having a progressively tapering profile, and FIG. 12D illustrates a braid structure 908 having a wing like cross section similar to a posterior leaflet profile shape.

In some embodiments, a braid structure may be finished by electro-polishing and/or passivation (e.g., using HF or $HNO_3$ acid, or other suitable acid). In some embodiments, a braid structure may be fitted with a covering and/or insert. For example, in embodiments where the braid density is low, a covering and/or insert may be added to enable the repair device to function to block regurgitant flow. A covering or insert may be formed from polyester, other polymer, or other suitable biocompatible material. In embodiments with sufficient braid density (e.g., sufficient to provide acceptable blockage of regurgitant flow, a covering and/or insert may be omitted.

In some embodiments, to prepare a repair device for loading onto or into a delivery device, the repair device may be stretched to an elongated and lower profile shape, cooled (e.g., using a liquid nitrogen spray and/or another suitable coolant and/or cooling process), and collapsed (e.g., through reversible martensitic deformation) into a delivery device, such as a delivery sheath or delivery catheter. In some embodiments, a funnel may be utilized to enable the repair device to be collapsed and directed into the delivery device.

Figures 13A, 13B:
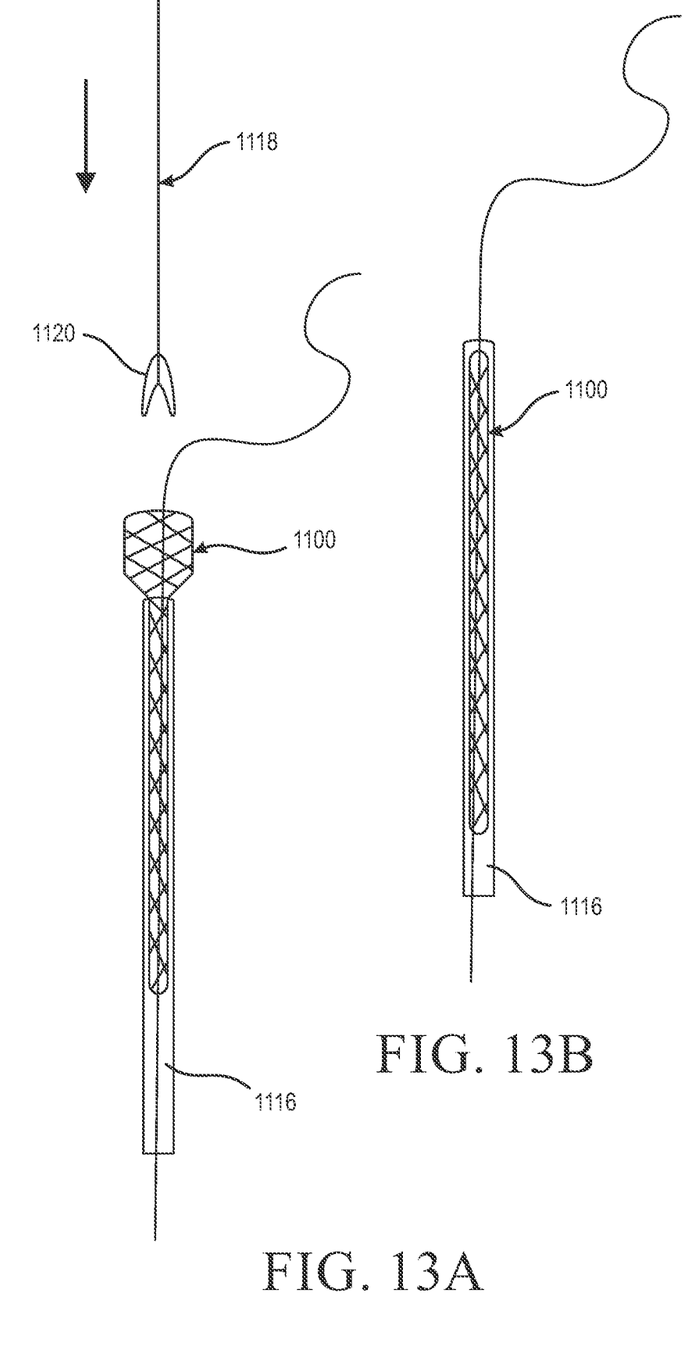
FIGS. 13A-13C illustrate the loading of a braid or wireframe structure into a delivery catheter as part of an exemplary loading process.
Figure 13C:
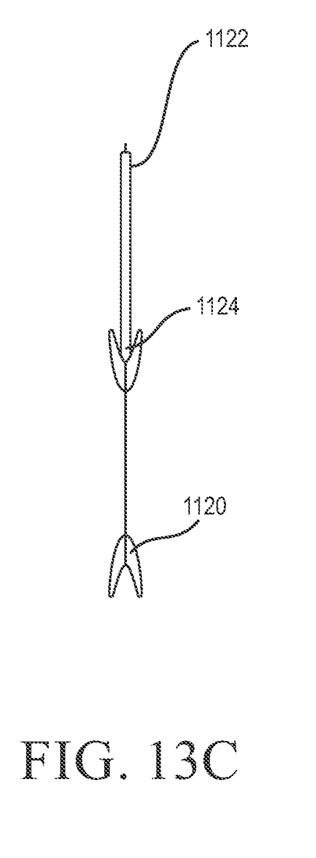

FIGS. 13A-13C illustrate an embodiment of a loading process for loading a repair device 1100 into a delivery catheter 1116 using a ratchet 118. In the illustrated embodiment, the ratchet 118 includes a clasp 1120 for engaging with the repair device 1100 to enable pushing of the repair device 1100 into the delivery catheter 1116 via pushing of the ratchet 1118. For example, the clasp 1120 may be configured to catch one or more wires/struts of the repair device 1100 to provide engagement with the repair device.

FIG. 13A illustrates the braid structure of the repair device 1100 partially positioned within the delivery catheter 1116, and FIG. 13B illustrates the repair device after being fully directed into the delivery catheter 1116. In some embodiments, the ratchet 1118 may remain in the delivery catheter 11116 to function as a pushing tool or pushing rod for the resulting delivery system.

FIG. 13C illustrates another embodiment of a ratchet 1122 having both a forward clasp 1120 for pushing a repair device, and a reverse clasp 1124 for engaging with one or more wires/struts of a repair device to enable the repair device to be pulled backwards and/or retracted through a delivery catheter.

As used herein, the term "vertical" refers to an orientation that is substantially perpendicular to a plane defined by a mitral valve annulus of a heart. As used herein, the term "horizontal" refers to an orientation that is substantially parallel to the plane defined by the mitral valve annulus of the heart.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a repair device of FIGS. 2B to 5 may be combinable with any element described in relation to a repair device delivery system of FIGS. 6A to 7C, unless clearly described otherwise.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A repair device to repair tissue at a native mitral valve, the repair device comprising:
    a body having a posterior section and an anterior section, the posterior section shaped to define an annular groove configured to receive tissue of a posterior portion of a native mitral valve; and
    an anchor extending anteriorly from the body and configured to engage tissue proximate an anterior portion of the native mitral valve to anchor the body against the posterior portion of the native mitral valve,
    wherein the body and the anchor together have a collapsed configuration for transfemoral delivery and an expanded configuration for deployment at the native mitral valve.

2. The repair device of claim 1, wherein the anchor includes an upper anchor section and a lower anchor section.

3. The repair device of claim 1, wherein the anchor includes at least one barb.

4. The repair device of claim 3, wherein the at least one barb is configured to enhance fixation of the anchor to tissue.

5. The repair device of claim 1, wherein the anchor is configured to allow movement of an anterior leaflet of the native mitral valve when the anchor is engaged with tissue proximate the anterior portion of the native mitral valve.

6. The repair device of claim 1, wherein the anchor is configured to stabilize the body against the posterior portion of the native mitral valve while minimizing septal directed forces when engaged with tissue proximate the anterior portion of the native mitral valve.

7. The repair device of claim 1, wherein the annular groove is configured to receive tissue of a posterior rim of the native mitral valve when the repair device is anchored at the native mitral valve.

8. The repair device of claim 1, wherein at least the body comprises a wire framework.

9. The repair device of claim 8, wherein the wire framework is formed from a superelastic wire material.

10. The repair device of claim 8, wherein the body further includes a cover disposed on the wire framework.

11. The repair device of claim 8, wherein the body further includes an insert integrated with the wire framework.

12. The repair device of claim 1, wherein the body is configured to enable an anterior leaflet of the native mitral valve to coapt against the body when anchored at the native mitral valve.

13. The repair device of claim 1, further comprising a tissue growth promoter disposed on at least a portion of the repair device to encourage tissue ingrowth.

14. The repair device of claim 1, wherein at least the body is formed of an expandable porous polymer.

* * * * *